United States Patent
Sugiyama et al.

(10) Patent No.: US 8,043,836 B2
(45) Date of Patent: Oct. 25, 2011

(54) PROCESS FOR PRODUCING AMINO ACID DERIVATIVE FROM HYDROXYIMINO ACID

(75) Inventors: Masakazu Sugiyama, Kanagawa (JP); Kunihiko Watanabe, Kanagawa (JP); Tadashi Takemoto, Kanagawa (JP); Kenichi Mori, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 898 days.

(21) Appl. No.: 11/576,421

(22) PCT Filed: Sep. 29, 2005

(86) PCT No.: PCT/JP2005/017962
§ 371 (c)(1),
(2), (4) Date: Nov. 1, 2007

(87) PCT Pub. No.: WO2006/038520
PCT Pub. Date: Apr. 13, 2006

(65) Prior Publication Data
US 2008/0193984 A1 Aug. 14, 2008

(30) Foreign Application Priority Data
Oct. 5, 2004 (JP) .................................. 2004-292987

(51) Int. Cl.
C12P 1/00 (2006.01)
C12P 13/04 (2006.01)
C12P 13/22 (2006.01)
C12P 17/10 (2006.01)
C07D 209/18 (2006.01)

(52) U.S. Cl. .......... 435/106; 435/41; 435/108; 435/121; 548/495

(58) Field of Classification Search ........................ None
See application file for complete search history.

(56) References Cited

U.S. PATENT DOCUMENTS

| | | |
|---|---|---|
| 7,064,219 B2 | 6/2006 | Kawahara et al. |
| 7,241,599 B2 | 7/2007 | Sugiyama et al. |
| 7,244,462 B2 | 7/2007 | Amino et al. |
| 7,329,427 B2 | 2/2008 | Amino et al. |
| 7,371,549 B2 | 5/2008 | Sugiyama et al. |
| 7,390,909 B2 | 6/2008 | Kawahara et al. |
| 7,396,941 B2 | 7/2008 | Mori et al. |
| 7,402,412 B2 | 7/2008 | Sugiyama et al. |
| 7,432,100 B2 | 10/2008 | Sugiyama et al. |
| 7,534,590 B2 | 5/2009 | Mori et al. |
| 7,534,898 B2 | 5/2009 | Amino et al. |
| 7,553,974 B2 | 6/2009 | Mori et al. |
| 7,612,214 B2 | 11/2009 | Amino et al. |
| 7,662,596 B2 | 2/2010 | Sugiyama et al. |
| 7,781,005 B2 | 8/2010 | Mori |
| 2005/0009153 A1 | 1/2005 | Sugiyama et al. |
| 2005/0020508 A1 | 1/2005 | Amino et al. |
| 2005/0153405 A1 | 7/2005 | Sugiyama et al. |
| 2005/0272939 A1 | 12/2005 | Amino et al. |
| 2006/0083695 A1 | 4/2006 | Mori |
| 2007/0072277 A1 | 3/2007 | Sugiyama et al. |
| 2008/0091032 A1 | 4/2008 | Kawahara et al. |
| 2008/0193975 A1 | 8/2008 | Sugiyama et al. |
| 2008/0199921 A1 | 8/2008 | Sugiyama et al. |
| 2008/0207920 A1 | 8/2008 | Kawahara et al. |
| 2008/0318290 A1 | 12/2008 | Sugiyama et al. |
| 2009/0259052 A1 | 10/2009 | Kawahara et al. |
| 2009/0318528 A1 | 12/2009 | Mori et al. |
| 2010/0184165 A1 | 7/2010 | Sugiyama et al. |

FOREIGN PATENT DOCUMENTS

| | | |
|---|---|---|
| JP | 4 234993 | 8/1992 |
| JP | 04234993 A * | 8/1992 |
| JP | 2003 171365 | 6/2003 |
| WO | 03 056026 | 7/2003 |
| WO | 03 059865 | 7/2003 |
| WO | 2004 018672 | 3/2004 |

OTHER PUBLICATIONS

U.S. Appl. No. 12/825,886, filed Jun. 29, 2010, Amino, et al.
U.S. Appl. No. 12/853,844, filed Aug. 10, 2010, Sugiyama, et al.
U.S. Appl. No. 07/178,323, filed Apr. 6, 1988, Amino, et al.
U.S. Appl. No. 12/613,839, filed Nov. 6, 2009, Sugiyama, et al.
105,696, filed Jun. 25, 2009, Kawahara, et al.
U.S. Appl. No. 12/768,360, filed Apr. 27, 2010, Sugiyama, et al.
U.S. Appl. No. 12/758,433, filed Apr. 12, 2010, Sugiyama, et al.

(Continued)

*Primary Examiner* — Chris R Tate
*Assistant Examiner* — Aaron Kosar
(74) *Attorney, Agent, or Firm* — Oblon, Spivak, McClelland, Maier & Neustadt, L.L.P.

(57) ABSTRACT

The present invention is to provide an industrially advantageous method for producing an amino acid derivative. Provided is a method for producing an amino acid derivative including contacting a microorganism and/or an enzyme with a hydroxyimino acid represented by the following general formula (I):

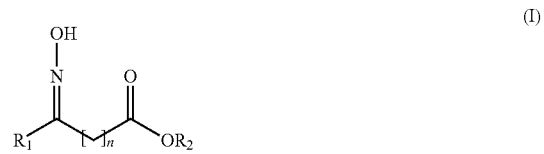

wherein $R_1$ represents an optionally substituted predetermined hydrocarbon group; $R_2$ represents a C1 to C3 alkyl group or a hydrogen atom; and n is 0 or 1, to produce an amino acid derivative represented by the following general formula (III):

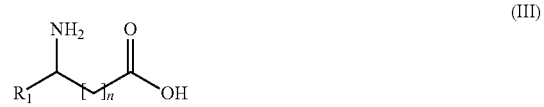

wherein $R_1$ and n have the same meanings as those of $R_1$ and n in the general formula (I), wherein the microorganism and/or the enzyme is capable of catalyzing the reaction.

31 Claims, No Drawings

OTHER PUBLICATIONS

Bernd Clement, et al., "Isolation and Characterization of the Protein Components of the Liver Microsomal O2-Insensitive NADH-Benzamidoxime Reductase", The Journal of Biological Chemistry, vol. 272, No. 31, pp. 19615-19620, 1997.

Don E. Gibbs, et al., "Asymmetric Synthesis of Amines by Action of Baker's Yeast on Oximes", Tetrahedron Letters, vol. 31, No. 39, pp. 5555-5558, 1990.

Larry A. Sternson, et al., "Species Variations in the Metabolism of Acetophenone Oxime by Hepatic Enzymes", Pharmacology, vol. 13, No. 3, pp. 234-240, 1975.

Bernd Clement, et al., "Enzymatic Reduction of Benzamidoxime to Benzamidine", Arch. Pharm. vol. 321, No. 12, pp. 955-956, 1988.

U.S. Appl. No. 12/613,713, filed Nov. 6, 2009, Kawahara, et al.

U.S. Appl. No. 13/081,024, filed Apr. 6, 2011, Amino, et al.

U.S. Appl. No. 13/044,618, filed Mar. 10, 2011, Sugiyama, et al.

* cited by examiner

PROCESS FOR PRODUCING AMINO ACID DERIVATIVE FROM HYDROXYIMINO ACID

CROSS REFERENCES TO RELATED APPLICATIONS

This application is a 371 of International Patent Application No. PCT/JP05/17962, filed on Sep. 29, 2005, and claims priority to Japanese Patent Application No. 2004-2929987, filed on Oct. 5, 2004.

TECHNICAL FIELD

The present invention relates to a method for producing an amino acid derivative from hydroxyimino acid, and, particularly to a method for producing an amino acid derivative from hydroxyimine acid by enzymatic reduction.

BACKGROUND ART

Amino acids are very important components in industries as, e.g., drugs, food, reagents, and chemical synthesis intermediates. Methods for producing an amino acid are roughly divided into four methods, i.e., an extraction method, a fermentation method, an enzyme method, and a chemical synthesis method. The enzyme method is a method in which a precursor having a similar structure to that of an objective amino acid as a starting material is converted at once into the amino acid through one to several stages of enzyme reaction. Generally, the enzyme method gives an amino acid having high purity with little amount of by-products. When the precursor serving as the substrate is available inexpensively, the enzyme method is a very efficient production method.

Monatin, one kind of amino acid derivative, is a natural occurring, sweet-tasting amino acid isolated and extracted from roots of shrubs in South Africa. Monatin has sweetness that is several ten times to thousand times stronger than that of sucrose, and is expected to be used as a sweetener.

As an example of a chemical synthesis method for producing monatin, there is a method wherein an indolacetic acid derivative and an aspartic acid halide are used as starting materials to synthesize a ketone derivative, and a cyanohydrin derivative is obtained therefrom, which is then hydrolyzed under basic conditions (for example, Patent Document 1). As an example of an enzyme method, there is a method wherein 4-(indol-3-ylmethyl)-4-hydroxy-2-oxoglutarate (also called IHOG) is formed as an intermediate from indol-3-pyruvic acid, and then monatin is produced therefrom in the presence of an enzyme (for example, Patent Document 2). There is also known a method for producing the aforementioned IHOG in the presence of an enzyme (for example, Patent Document 3).

As another method for forming monatin from IHOG, there is a method wherein IHOG is used to produce IHOG-oxime (or 4-hydroxy-4-(3-indolylmethyl)-2-hydroxyiminoglutarate) which is then converted into monatin in the presence of a reducing catalyst such as rhodium (for example, Patent Document 4). However, there is not known any method for producing monatin from IHOG-oxime which is more stable than IHOG, in the presence of a microorganism or an enzyme.

Reduction of oxime (hydroxyimine) by a microorganism or an enzyme (enzymatic reduction) is described in Patent Document 5 and Nonpatent Documents 1 to 4. For example, the Patent Document 5 describes a method for producing α-methylbenzylamine from acetophenone oxime. However, there is not known any method for reducing hydroxyimino acid in the presence of a microorganism or an enzyme to produce an amino acid.

LIST OF THE CITED REFERENCES

Patent Document 1: Japanese Patent Application Laid-open No. 2003-171365
Patent Document 2: International Publication WO2003/056026 Pamphlet
Patent Document 3: International Publication WO2004/018672 Pamphlet
Patent Document 4: International Publication WO2003/059865 Pamphlet
Patent Document 5: Japanese Patent Application Laid-open No. H4-234993 A
Nonpatent Document 1: Pharmacology, 13, 234 (1975)
Nonpatent Document 2: Clement et al., Arch.der Parmazie, 321, 955 (1998)
Nonpatent Document 3: Clement et al., JBC, 272, 19615 (1997)
Nonpatent Document 4: Gibbs et al., Tetrahedron Lett., 31, 5555-5558 (1990)

DISCLOSURE OF INVENTION

Problem to be Solved by the Invention

The method for producing an amino acid derivative by chemical synthesis is useful for producing an amino acid derivative whose isolation and extraction is difficult. However, the chemical synthesis has many disadvantages in terms of cost on the industrial production scale, such as high equipment expenses and necessity for use of an expensive catalyst. On the contrary, the method of using a microorganism or an enzyme is industrially useful in many cases in order to produce an amino acid derivative. Under these circumstances, there is an object of the present invention to provide an industrially-advantageous method for producing an amino acid derivative.

Means for Solving Problem

The present inventors have conducted extensive studies on a new method for producing an amino acid derivative such as monatin. As a result, they have found a method for producing an amino acid derivative by reducing a hydroxyimino acid using a microorganism and/or an enzyme, to thereby complete the present invention. That is, the present invention provides the following method for producing an amino acid derivative.

(1) A method for producing an amino acid derivative, the method comprising the step of: contacting a microorganism and/or an enzyme with a hydroxyimino acid represented by the following general formula (I):

wherein $R_1$ represents a substituent selected from an optionally substituted C2 to C6 alkyl group, an optionally substituted C6 to C14 aryl group, an optionally substituted C6 to C10 cycloalkyl group, an optionally substituted C7 to C19 aralkyl group, an optionally substituted C2 to C10 alkoxyalkyl group, an optionally substituted group which is identical with any one of the foregoing groups except for containing a heteroatom in the carbon skeleton thereof, and a substituent $R_3$ represented by the following general formula (II):

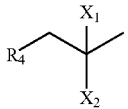
(II)

wherein $R_4$ represents a substituent selected from an optionally substituted C2 to C6 alkyl group, an optionally substituted C6 to C14 aryl group, an optionally substituted C6 to C10 cycloalkyl group, an optionally substituted C7 to C19 aralkyl group, an optionally substituted C2 to C10 alkoxyalkyl group, and an optionally substituted group which is identical with any one of the foregoing groups except for containing a heteroatom in the carbon skeleton thereof; $X_1$ and $X_2$ independently represent a hydroxyl group or a carbonyl group, $R_2$ represents a C1 to C3 alkyl group or a hydrogen atom; and n is 0 or 1, to produce an amino acid derivative represented by the following general formula (III):

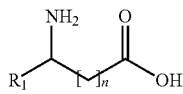
(III)

wherein $R_1$ and n have the same meanings as those of $R_1$ and n in the general formula (I), wherein the microorganism and/or the enzyme is capable of catalyzing the reaction.

(2) The method according to (1), wherein n is 0, and the amino acid derivative produced thereby is an α-amino acid derivative.

(3) The method according to (1), wherein the amino acid derivative produced thereby is an α-L-amino acid.

(4) The method according to (1), wherein the amino acid derivative produced thereby is an α-D-amino acid.

(5) The method according to (1), wherein n is 1, and the amino acid derivative produced thereby is a β-amino acid derivative.

(6) The method according to (1), wherein the aryl group is an optionally substituted phenyl or naphthyl group.

(7) The method according to (1), wherein the aralkyl group is an optionally substituted phenylalkyl or naphthylalkyl group.

(8) The method according to (1), wherein the group containing a heteroatom in the carbon skeleton is an optionally substituted pyridyl or indolyl group.

(9) A method for producing monatin comprising the step of contacting a microorganism and/or an enzyme with IHOG-oxime represented by the general formula (IV):

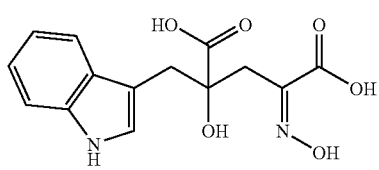
(IV)

to produce monatin represented by the following general formula (V):

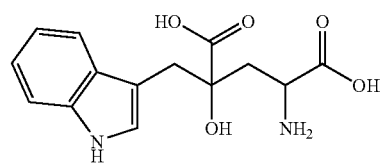
(V)

wherein the microorganism and/or the enzyme is capable of catalyzing the reaction.

(10) A method for producing β-phenyl-β-alanine, comprising the step of contacting a microorganism and/or an enzyme with BAE-oxime represented by the general formula (VI):

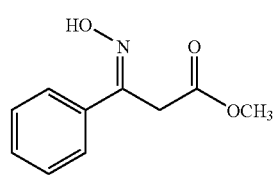
(VI)

to produce β-phenyl-β-alanine, wherein the microorganism and/or the enzyme is capable of catalyzing the reaction.

(11) A method for producing tryptophan, comprising the step of contacting a microorganism and/or an enzyme with indol-3-pyruvate-oxime represented by the general formula (VII):

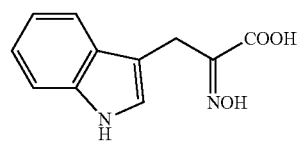
(VII)

to produce tryptophan, wherein the microorganism and/or the enzyme is capable of catalyzing the reaction.

(12) The method according to any one of (1), (9), (10) and (11), wherein the microorganism is one or more species of microorganisms belonging to any genera selected from the group consisting of the genera *Citrobacter*, *Escherichia*, and *Rhodococcus*.

(13) The method according to any one of (1), (9), (10) and (11), wherein the microorganism is selected from the group consisting of *Citrobacter freundii*, *Escherichia intermedia*, *Escherichia coli*, and *Rodococcus marinonascens*.

(14) The method according to any one of (1), (9), (10) and (11), wherein one or more compounds selected from the group consisting of NADH, NADPH, pyridoxal-5'-phosphate, and $MgCl_2$ are added to a reaction solution for producing the compound represented by the general formula (III) from the compound represented by the general formula (I).

Effect of the Invention

According to the present invention, there is provided a method for readily producing amino acid, which is advantageous in terms of the cost.

BEST MODE(S) FOR CARRYING OUT THE INVENTION

In the method for producing an amino acid derivative according to the present invention, the hydroxyimino acid of the general formula (I) is converted into the compound of the general formula (III) by the catalytic action of a microorganism and/or enzyme. In this specification, the "amino acid derivative" encompasses both an amino acid itself and derivatives thereof.

Preferable examples of the microorganism having an ability to catalyze this reaction for use in the present invention may include microorganisms belonging to any of genera selected from the group consisting of the genera *Citrobacter, Escherichia, Corynebacterium, Rhodococcus, Salmonella,* and *Erwinia*. More preferable examples of the microorganism may include *Citrobacter freundii, Citrobacter intermedius, Escherichia intermedia, Escherichia coli, Corynebacterium equi, Rohodococcus marinonascens, Salmonella* sp., *Erwinia amylovora*, and *Salmonella enteritidis*.

More specifically, as preferable microorganisms, the following strains may be exemplified. The strain names thereof and depositary authorities are as follows:

(1) *Citrobacter freundii* IFO 13546
(i) Deposition Number: IFO 13546
(iii) Depositary authority (Address): NITE Biological Resource Center, National Institute of Technology and Evaluation (2-5-8 Kazusakamatari, Kisarazu-shi, Chiba 292-0818, Japan).

(2) *Escherichia intermedia* AJ 2607
(i) Deposition Number: FERM BP-10401 (transferred from FERM P-20215)
(ii) Original deposition date: Sep. 8, 2004
(iii) Depositary authority (Address): International Patent Organism Depositary, National Institute of Advanced Industrial Science and Technology (Central 6, 1-1-1 Higashi, Tsukuba, Ibaraki 305-8566, Japan).

(3) *Escherichia coli* ATCC 13070
(i) Deposition Number: ATCC 13070
(iii) Depositary authority (Address): American Type Culture Collection, P.O. Box 1549 Manassas, Va. 20110, USA (4) *Escherichia coli* ATCC 12814
(i) Deposition Number: ATCC 12814
(iii) Depositary authority (Address): American Type Culture Collection, P.O. Box 1549 Manassas, Va. 20110, USA (5) *Rhodococcus marinonascens* AJ110354
(i) Deposition Number: FERM BP-10400 (transferred from FERM P-20213)
(ii) Original deposition date: Sep. 8, 2004
(iii) Depositary authority (Address): International Patent Organism Depositary, National Institute of Advanced Industrial Science and Technology (Central 6, 1-1-1 Higashi, Tsukuba, Ibaraki 305-8566, Japan).

The enzyme used in the present invention can be isolated and purified from the aforementioned microorganisms or the like. The phrase "in the presence of a microorganism and/or an enzyme" refers to an operation to make the microorganism and/or the enzyme present in the reaction system for converting the hydroxyimino acid represented by the general formula (I) into the amino acid derivative represented by the general formula (III). "The microorganism and/or the enzyme" is not particularly limited with respect to its origin, preparation method and the like insofar as it has the desired activity for the present invention. As the microorganism, it is possible to employ not only the aforementioned microorganisms catalyzing the reaction of the present invention, but also host microorganisms transformed with a gene (including a recombinant gene) encoding an enzyme catalyzing the reaction, or enzymes produced by such host microorganisms. That is, the microorganism and/or the enzyme may be present in any forms in the reaction system insofar as the hydroxyimino acid represented by the general formula (I) is converted into the amino acid derivative represented by the general formula (III). Either the microorganism or the enzyme, or both, may be used.

"The microorganism and/or the enzyme" for use in the production method of the present invention may have the following forms. Examples of the specific forms may include a cultured product of the microorganism, microbial cells separated from the cultured product, and a material obtained by treating the microbial cells. The cultured product of the microorganism is a material obtained by culturing the microorganism, and may specifically be a mixture containing microbial cells, a broth which has been used in cultivation of the microorganism and substances produced by the microorganism. The microbial cells may be washed and used as washed microbial cells. The material obtained by treating the microbial cells may include materials obtained by disrupting, lysing or lyophilizing the microbial cells, as well as a crude enzyme recovered after treatment of the microbial cells. The material obtained by treating the microbial cells may also include a purified enzyme obtained by further purifying the crude enzyme. The purified enzyme may include a partially purified enzyme obtained by any of wide variety of purification methods, and an immobilized enzyme, i.e., the enzyme which has been immobilized by covalent bonding, adsorption, inclusion or the like. Some of the microorganisms used are partially lysed during cultivation. In this case, the supernatant of the broth may also be used as "the microorganism and/or the enzyme" described above.

"The microorganism and/or the enzyme" for use in the production method of the present invention may also include a genetically-engineered strain that expresses an enzyme for converting the hydroxyimino acid represented by the general formula (I) into the amino acid derivative represented by the general formula (III); a material obtained by treating such microbial cells, the treatment including an acetone-treatment and a lyophilization; and immobilized microbial cells or an immobilized microbial treated material which have been immobilized by covalent bonding, adsorption, inclusion or the like.

The production method of the present invention includes reaction of the hydroxyimino acid of the general formula (I) as the starting material. Specific examples of $R_1$ in the general formula (I) may include the following groups.

Specific examples of the C2 to C6 alkyl group as $R_1$ may include ethyl group, n-propyl group, isopropyl group, n-butyl group, isobutyl group, sec-butyl group, tert-butyl group, n-pentyl group, isopentyl group, neopentyl group, n-hexyl group, and isohexyl group.

Specific examples of the C6 to C14 aryl group as $R_1$ may include phenyl group, tolyl group, xylyl group, biphenyl group, naphthyl group, anthryl group and phenanthryl group, and preferably phenyl group, and naphthyl group.

Specific examples of the C6 to C10 cycloalkyl group as $R_1$ may include cyclohexyl group, cycloheptanyl group, cyclooctanyl group, cyclononanyl group, and cyclodecanyl group.

Specific examples of the C7 to C19 aralkyl group as $R_1$ may include phenylalkyl group such as benzyl group, benzhydryl group, phenethyl group and trityl group, cinnamyl group, styryl group, and naphthyl group, and preferably phenylalkyl group and naphthylalkyl group.

Specific examples of the C2 to C11 alkoxyalkyl group as $R_1$ may include C1 to C10 alkyl groups which are substituted with a group selected from methoxy group, ethoxy group, propoxy group, isopropoxy group, butoxy group, pentyloxy group, phenoxy group, heptoxy group, octoxy group, nonanoxy group, decanoxy group, and undecoxy group.

One embodiment of the group containing a heteroatom in a carbon skeleton of the foregoing group as $R_1$ may be a heterocycle-containing hydrocarbon group. The "heterocycle-containing hydrocarbon group" is a cyclic hydrocarbon group wherein a heteroatom is incorporated in a ring of a cyclic compound. The heterocycle-containing hydrocarbon group may be a heteroaryl group. The heterocycle-containing hydrocarbon group is not limited by the presence or absence of aromaticity. The heterocycle-containing hydrocarbon group may be monocyclic or polycyclic. Specific examples of the heterocycle-containing hydrocarbon group may include furyl group, thienyl group, pyridyl group, piperidyl group, piperidino group, morpholino group, indolyl group, and alkyl groups substituted with any of the aforementioned heterocyclic groups, and preferable examples thereof may include pyridyl group and indolyl group.

$R_1$ mentioned above may be further substituted with at least one substituent selected from a halogen atom, a hydroxyl group, a C3 or less alkyl group, a C3 or less alkoxy group, and an amino group.

$R_2$ represents a C1 to C3 alkyl group or a hydrogen atom. Examples of the C1 to C3 alkyl group may include ethyl group, methyl group, n-propyl group, and isopropyl group.

Alkyl group, aryl group, cycloalkyl group, aralkyl group, alkoxyalkyl group, a group containing a heteroatom in a carbon skeleton of the foregoing groups, and a substituent which the foregoing groups may have for the examples of $R_4$ may include the same as those for $R_1$ mentioned above.

The compound represented by the general formula (I) can be obtained by various reactions for producing oxime, that is, reactions for converting a CO group corresponding to a hydroxyimino group into a CNOH group. Specifically, the compound (I) is obtainable by the methods described in International Publication No. WO2003/056026 pamphlet, No. WO2004/018672 pamphlet, and No. WO2003/059865 pamphlet.

The method for producing oxime (conversion for producing hydroxyimino group) may be carried out by reacting an amine compound represented by the following general formula (VIII) or a salt thereof:

$$H_2N—OR_5 \quad (VIII)$$

(wherein $R_5$ represents a hydrogen atom, an alkyl group, an aryl group, or an aralkyl group) with a corresponding keto compound under neutral or alkaline conditions. When $R_5$ is an alkyl group, an aryl group, or an aralkyl group, $R_5$ is preferably a C1 to C3 alkyl, aryl or aralkyl group. In terms of crystallization, $R_5$ is preferably selected from methyl group and benzyl group.

The method for producing oxime may be readily performed with a hydroxylamine of the general formula (VIII) wherein $R_5$ is a hydrogen atom. As an example, oxime may be produced by adding hydroxylamine hydrochloride to a keto compound-containing solution under neutral or weakly alkaline conditions, and then stirring the solution for 0.5 to 60 hours under the condition of room temperature to about 10° C. The reaction of conversion for producing oxime may be carried out preferably at pH 6 to 10, more preferably at pH 7 to 9. The conditions for the reaction of converting the keto compound into the corresponding oxime are not particularly limited, and the reaction conditions for conversion of producing oxime may be determined through a simple preliminary examination by those skilled in the art.

In the production method of the present invention, the compound represented by the general formula (I) is converted into the product compound represented by the general formula (III). The definitions of $R_1$, n and others in the general formula (III) are the same as those for the aforementioned general formula (I).

When n is 0 in the general formula (I), an α-amino acid derivative is obtained as the compound of the general formula (III). When n is 1, a β-amino acid derivative is obtained. By, e.g., selecting an L- or D-compound of the general formula (I), an L- or D-compound of the general formula (III) may be produced. When the compound (III) is obtained as a mixture of L and D compounds, either one of them may be isolated and purified from the mixture.

The conditions of the reaction system for using the microorganism and/or the enzyme may be suitably adjusted depending on specific types of the microorganism, enzyme, and starting materials to be used. The amount of the microorganism and/or the enzyme for use may be an amount to exhibit the objective effect (effective amount). The effective amount can be easily determined in a simple preliminary experiment by those skilled in the art. For example, when the enzyme is used, preferable amount thereof may be about 0.01 to 100 units (U). When the washed microorganism is used, preferable amount thereof may be about 0.1 to 500 g/L. The reaction is usually carried out at a temperature at which the enzyme used is active, preferably in the range of 10 to 50° C., more preferably 20 to 40° C., and still more preferably 25 to 37° C. The pH value of the enzyme reaction solution is regulated usually in the range of 2 to 12, preferably 7 to 11, more preferably 8 to 9.

In a preferable embodiment of the production method of the present invention, one or more compounds selected from the group consisting of NADH, NADPH, pyridoxal-5'-phosphate (which may be referred to hereinafter as PLP), and $MgCl_2$ may be added. By adding these additives, the amount of the produced amino acid derivative represented by the general formula (III) can be increased.

The combination of the four additives may be suitably selected depending on the type of microorganism or the like. Preferable combination thereof may be the combination containing at least three additives: NADH, NADPH, and PLP, and more preferably a combination containing all of the four additives. Preferable amount of each additive in the reaction solution is as follows: The amount of NADH is preferably 0.01 to 200 mM, more preferably 0.1 to 50 mM; the amount of NADPH is preferably 0.01 to 200 mM, more preferably 0.1 to 50 mM; the amount of $MgCl_2$ is preferably 0.01 to 10 mM, more preferably 0.1 to 1 mM; and the amount of PLP is preferably 0.01 to 10 mM, more preferably 0.1 to 1 mM.

The production method of the present invention is preferable for producing an amino acid derivative, wherein $R_1$ is an aromatic ring or a heterocycle-containing group, and is applied more preferably to production of monatin, tryptophan, phenylalanine, or the like. For production of monatin, IHOG-oxime is used as the compound represented by the general formula (I). For production of tryptophan, IPA-oxime (indol-3-pyruvate-oxime) is used as the compound represented by the general formula (I). For production of β-phenyl-β-alanine, BAE-oxime (3-hydroxyimino-3-phenyl-propionic acid methyl ester) is used as the compound represented by the general formula (I). BAE is an abbreviation of benzoyl acetate ethyl ester.

EXAMPLES

The present invention will be described in detail with reference to the following Examples, although the present invention is not limited thereto.

In the Examples, quantification of monatin was carried out by high performance liquid chromatography with INERTSIL ODS-80 Å, octadecyl bound silica, (5 μm, 6×150 mm) manufactured by GL Sciences, Inc. The analysis conditions are as shown below.

Mobile phase: 12% (v/v) acetonitrile/0.05% (v/v) aqueous trifluoroacetic acid;
Flow rate: 1.5 ml/min;
Column temperature: 30° C.; and
Detection: UV 210 nm.

Under the aforementioned analysis conditions, (2S,4S)-monatin and (2R,4R)-monatin can be fractionated and quantified at a retention time of 12.1 minutes, and (2S,4R)-monatin and (2R,4S)-monatin at a retention time of 9.7 minutes.

Where necessary, analysis by high performance liquid chromatography with an optical resolution column CROWNPAK CR(+) (4.6×150 mm) (manufactured by Daicel Chemical Industries, Ltd.) was also conducted. The analysis conditions are as shown below.

Mobile phase: Aqueous perchloric acid (pH 1.5)/10% (v/v) methanol;
Flow rate: 0.5 ml/min;
Column temperature: 30° C.; and
Detection: UV 210 nm.

Under the aforementioned analysis conditions, the monatin optical isomers can be fractionated and quantified in the order of (2S,4S), (2R,4R), (2S,4R) and (2S,4S) at retention times of 42, 57, 64, and 125 minutes respectively.

Production Example 1

Production of IHOG-oxime Diammonium Salt (4-hydroxy-4-(3-indolylmethyl)-2-hydroxyiminoglutarate Diammonium Salt)

73.8 g (352 mmol) of indol-3-pyruvic acid was added to and dissolved in 917 g of 1.6 wt % aqueous sodium hydroxide. The temperature of the reaction solution was adjusted to 35° C. While the pH of the solution was kept at 11.1 with 30% aqueous sodium hydroxide, 310.2 g (1761 mmol) of 50% aqueous pyruvic acid was added dropwise over 2 hours. The reaction mixture was further reacted for 4.5 hours to obtain a reaction solution containing 4-hydroxy-4-(3-indolylmethyl)-2-ketoglutaric acid. While the pH of this reaction solution was kept at 7 with 30% aqueous sodium hydroxide, 367.2 g (2114 mmol) of 40% aqueous hydroxylamine hydrochloride was added thereto, and the mixture was stirred at 5° C. for 17.5 hours. The pH value of the reaction solution was adjusted to 2 with concentrated hydrochloric acid, and its organic matter was then extracted with ethyl acetate. The organic layer was washed with saturated saline and then concentrated to obtain residues. The residues were subjected to recrystallization from 60 ml of 28% ammonia water and 1350 ml of 2-propanol to obtain 43.4 g of 4-hydroxy-4-(3-indolylmethyl)-2-hydroxyiminoglutarate diammonium salt (142 mmol: yield 40% relative to indol-3-pyruvic acid) as crystals.

Production Example 2

Production of IHOG-oxime Dipotassium Salt (4-hydroxy-4-(3-indolylmethyl)-2-hydroxyiminoglutarate Dipotassium Salt)

10 g of 4-hydroxy-4-(3-indolylmethyl)-2-hydroxyiminoglutarate diammonium salt produced in accordance with Production Example 1 was dissolved in 20 ml water and then passed through a 100 ml of cation exchange resin DIAION PK228 (potassium-type, manufactured by Mitsubishi Chemical Corporation), for converting the compound into desired ion. The eluate was concentrated into 20 g concentrate to obtain an aqueous solution of 4-hydroxy-4-(3-indolylmethyl)-2-hydroxyiminoglutarate dipotassium salt.

Production Example 3

Production of Indolpyruvate Oxime 4.06 g (0.02 mol) of indolpyruvic acid and 1.32 g (0.02 mol) of 85% potassium hydroxide were dissolved in 50 ml water, and 1.53 g (0.022 mol) of hydroxylamine hydrochloride was added thereto. 1.45 g (0.022 mol) of 85% potassium hydroxide was further added thereto and the mixture was stirred overnight at room temperature. The reaction solution was adjusted to pH 2 with hydrochloric acid, and the precipitated crystals were collected by filtration. The resulting wet crystals were dried to obtain 3.34 g of indolpyruvate oxime. The yield of the product relative to indolpyruvic acid was 76.5%, and a signal of ESI-MS:219.1 [M+H]$^+$ was obtained.

Production Example 4

Production of Benzoyl Acetate Ethyl Ester Oxime 3.84 (0.02 mol) of benzoyl acetate ethyl ester was dissolved in 50 ml of MeOH, and 1.53 g (0.022 mol) of hydroxylamine hydrochloride was added thereto. 2.23 g (0.022 mol) of triethylamine was added thereto, and the mixture was stirred overnight at room temperature. The reaction solution was concentrated under reduced pressure. Then water was added to the residues, and the precipitated crystals were collected by filtration. 3.27 g dried benzoyl acetate ethyl ester oxime was thereby obtained. The yield relative to the benzoyl acetate ethyl ester was 78.9%, and a signal of ESI-MS:208.2 [M+H]$^+$ was obtained.

Analysis Conditions)
Guard column: SHODEX IC YK-G, carboxyl-modified silica, (Showa Denko K.K.)
Column: SHODEX IC YK-421, carboxyl-modified silica, (Showa Denko K.K.)
Detection: Conductometric detector
Eluent: 4 mM phosphoric acid+5 mM 18-Crown-6
Flow rate: 0.6 ml/min
Analysis temperature: 40° C.

Example 1

Screening for IHOG-oxime-Reducing Microorganism

Screening for a microbial strain having an activity of reducing 4-hydroxy-4-(3-indolylmethyl)-2-hydroxyiminoglutaric acid (IHOG-oxime), i.e. a strain which produces monatin from substrate IHOG-oxime, was performed.

A sample microorganism (bacteria or yeast) was inoculated into a bouillon plate (manufactured by Eiken Chemical Co., Ltd.) and cultured at 30° C. for 24 hours. The resulting culture was inoculated into a plate containing 0.5 g/dl glycerol, 0.5 g/dl fumaric acid, 0.3 g/dl yeast extract, 0.2 g/dl peptone, 0.5 g/dl ammonium sulfate, 0.3 g/dl K$_2$HPO$_4$, 0.1 g/dl KH$_2$PO$_4$, 0.05 g/dl MgSO$_4$.7H$_2$O, 0.2 g/dl IHOG-oxime diammonium salt, and 2 g/dl agar powder (pH 6.5). The microorganism was then cultured at 30° C. for 24 hours. The resulting microorganism cells were inoculated into each of the following two reaction solutions such that the weight of the resulting wet microorganism cells became about 1% (w/v), and then the reaction mixture was reacted at 30° C. for 24 hours.

Reaction solution 1: 100 mM Tris-HCl (pH 8.0), 50 mM IHOG-oxime diammonium salt, 1 mM $MgCl_2$, 1 mM pyridoxal-5'-phosphate (PLP), 20 mM NADH, 20 mM NADPH, and 1% (v/v) toluene Monatin thus produced was then analyzed by TLC. 1 μl of the reaction solution was spotted on TLC plate silica gel 60F254 (manufactured by Merck) and thus obtained plates were dipped into a solution consisting of n-butanol:acetic acid:water (=4:1:2) and colored with ninhydrin. Monatin can be detected as a pink spot at a position with an Rf of approximately 0.39.

The reaction solution in which generation of monatin had been recognized was then analyzed by HPLC for quantitative analysis of generated monatin. As a result, generation of monatin with the strains shown in Table 1 was recognized. That is, monatin was produced from IHOG-oxime by microbial conversion.

TABLE 1

Monatin formed from IHOG-oxime
Reaction solution 1

| Strains | | Monatin generated (mM) |
|---|---|---|
| Citrobacter freundii | IFO 13546 | 3.2 |
| Escherichia intermedia | AJ 2607 | 3.2 |
| Escherichia coli | ATCC 13070 | 2.1 |
| Rhodococcus marinonascens | AJ 110354 | 1.2 |
| Escherichia coli | ATCC 12814 | 0.8 |

Example 2

Production of Monatin from Substrate IHOG-oxime Dipotassium Salt

The strains shown in Table 2 were used to conduct conversion of the substrate IHOG-oxime dipotassium salt. The method for preparing the microorganism cells was carried out in the same manner as in Example 1. As the reaction solution, the reaction solutions 2 and 3 shown below were used. After reaction at 30° C. for 24 hours, the amount of produced monatin was quantitatively determined by HPLC. As a result, as shown in Table 2, it was confirmed that monatin was produced also from IHOG-oxime dipotassium salt. From comparison between the reaction solutions 3 and 4, it was found that the amount of produced monatin was increased by adding NADH, NADPH, $MgCl_2$, pyridoxal-5'-phosphate (PLP) or the like to the reaction solution.

Reaction solution 2: 100 mM glycine-NaOH (pH 9.0), 50 mM IHOG-oxime dipotassium salt, 1 mM $MgCl_2$, 1 mM pyridoxal-5'-phosphate (PLP), 25 mM NADH, 25 mM NADPH, and 1% (v/v) toluene Reaction solution 3: 100 mM glycine-NaOH (pH 9.0), 50 mM IHOG-oxime dipotassium salt, and 1% (v/v) toluene

TABLE 2

Amount of monatin (mM) produced from substrate IHOG-oxime dipotassium salt

| Strain | | Reaction Solution 2 | Reaction Solution 3 |
|---|---|---|---|
| Citrobacter freundii | IFO 13546 | 11.30 | 6.47 |
| Escherichia intermedia | AJ 2607 | 11.65 | 6.79 |
| Escherichia coli | ATCC 13070 | 1.01 | 0.54 |

Example 3

Effect of Additional PLP, $MgCl_2$, NAD(P)H

The effect of addition of PLP, $MgCl_2$, and NAD(P)H on reduction reaction of IHOG-oxime by Citrobacter freundii IFO13546 and Escherichia intermedia AJ2607 was examined.

Reaction solutions (reaction solutions 4 to 9) having the compositions shown in Table 3 were prepared and used to carry out the reduction reaction of IHOG-oxime in the same manner as in Example 1, and monatin produced thereby was quantified.

The results (Table 4) indicated that the amount of monatin produced with the respective strains was increased by adding PLP, $MgCl_2$, or NAD(P)H.

Monatin produced with the reaction solution 4 was identified with an optical resolution column CROWNPAK CR(+). As a result, the product was revealed to be (2S,4S)-monatin.

TABLE 3

Reaction solution composition (unit: mM)

| | Reaction Solution 4 | Reaction Solution 5 | Reaction Solution 6 | Reaction Solution 7 | Reaction Solution 8 | Reaction Solution 9 |
|---|---|---|---|---|---|---|
| Glycine-NaOH (9.0) | 100 | 100 | 100 | 100 | 100 | 100 |
| IHOG-oxime.2K | 50 | 50 | 50 | 50 | 50 | 50 |
| NADH | 25 | 25 | 25 | 25 | 0 | 0 |
| NADPH | 25 | 25 | 25 | 25 | 0 | 0 |
| $MgCl_2$ | 1 | 0 | 1 | 0 | 1 | 0 |
| PLP | 1 | 1 | 0 | 0 | 1 | 0 |

TABLE 4

Amount of produced monatin (mM)

| | E. intermedia | C. freundii |
|---|---|---|
| Reaction Solution 4 | 11.6 | 11.3 |
| Reaction Solution 5 | 10.9 | 5.7 |
| Reaction Solution 6 | 1.2 | 5.2 |
| Reaction Solution 7 | 0.4 | 7.8 |

TABLE 4-continued

| Amount of produced monatin (mM) | | |
|---|---|---|
| | E. intermedia | C. freundii |
| Reaction Solution 8 | 6.8 | 6.5 |
| Reaction Solution 9 | 2.5 | 5.8 |

Example 4

Production of Tryptophan (Trp) from IPA-oxime (indol-3-pyruvate-oxime)

Each of *Citrobacter freundii* IFO 13546 and *Escherichia intermedia* AJ 2607 was inoculated into a bouillon plate (manufactured by Eiken Chemical Co., Ltd.) and cultured at 30° C. for 24 hours. The resulting culture was inoculated into a plate containing 0.5 g/dl glycerol, 0.5 g/dl fumaric acid, 0.3 g/dl yeast extract, 0.2 g/dl peptone, 0.5 g/dl ammonium sulfate, 0.3 g/dl $K_2HPO_4$, 0.1 g/dl $KH_2PO_4$, 0.05 g/dl $MgSO_4 \cdot 7H_2O$, 0.2 g/dl IHOG-oxime diammonium salt, and 2 g/dl agar powder (pH 6.5). The microorganism was then cultured at 30° C. for 24 hours. The resulting microorganism cells were inoculated into the following reaction solution 10 such that the weight of the wet microorganism cells became about 1% (w/v), and then the reaction mixture was reacted at 30° C. for 24 hours.

Reaction solution 10: 100 mM glycine-NaOH (pH 9.0), 50 mM IPA-oxime, 1 mM $MgCl_2$, 1 mM pyridoxal-5'-phosphate (PLP), 25 mM NADH, 25 mM NADPH, and 1% (v/v) toluene Qualitative analysis of generated tryptophan was performed with TLC. 1 µl of the reaction solution was spotted on TLC plate silica gel 60F254 (manufactured by Merck) and thus obtained plates were dipped into a solution consisting of n-butanol:acetic acid:water (=4:1:2) and colored with ninhydrin. Tryptophan can be detected as a purple spot at a position with an Rf of approximately 0.52.

The reaction solution in which generation of tryptophan had been recognized was then analyzed by HPLC for quantitative analysis of generated tryptophan. As a result, generation of tryptophan was recognized. That is, tryptophan was produced from IPA-oxime by conversion with the microorganisms.

(Analysis Conditions)
Column: Inertsil ODS-80A (GL Sciences, Inc.)
Detection: UV210 nm
Eluent: 12% (v/v) acetonitrile/0.05% aqueous trifluoroacetic acid
Flow rate: 1.5 ml/min
Analysis temperature: 30° C.

TABLE 5

| Amount of produced Trp | | |
|---|---|---|
| | E. intermedia | C. freundii |
| Produced Trp (mM) | 2.0 | 2.2 |

Example 5

Production of β-phenyl-β-alanine (β-Phe) from BAE-oxime

*Citrobacter freundii* IFO 13546 and *Escherichia intermedia* AJ 2607 were used as test strains, and each of the resulting microorganism cells obtained in the same manner as in Example 4 were inoculated into the following reaction solution 11 such that the weight of the wet microorganism cells became about 1% (w/v), and then the reaction mixture was reacted at 30° C. for 24 hours.

Reaction solution 11: 100 mM glycine-NaOH (pH 9.0), 50 mM BAE-oxime, 1 mM $MgCl_2$, 1 mM pyridoxal-5'-phosphate (PLP), 25 mM NADH, 25 mM NADPH, and 1% (v/v) toluene Qualitative analysis of the generated product was performed with TLC. 1 µl of the reaction solution was spotted on TLC plate silica gel 60F254 (manufactured by Merck) and thus obtained plates were dipped into a solution consisting of n-butanol:acetic acid:water (=4:1:2) and colored with ninhydrin. β-Phenyl-β-alanine ethyl ester can be detected as a yellow spot at a position with an Rf of approximately 0.72, and β-phenyl-β-alanine can be detected as a brown spot at a position with an Rf of approximately 0.51. As a result, a spot in the vicinity with the same Rf as that of β-phenyl-β-alanine was recognized.

The reaction solution in which generation of β-phenyl-β-alanine had been recognized was then analyzed by HPLC. As a result, generation of β-phenyl-β-alanine was recognized. That is, β-phenyl-β-alanine was produced from BAE-oxime by conversion with the microorganisms.

(Analysis Conditions)
Column: Inertsil ODS-80A (GL Sciences, Inc.)
Detection: UV210 nm
Eluent: 12% (v/v) acetonitrile/0.05% aqueous trifluoroacetic acid
Flow rate: 1.5 ml/min
Analysis temperature: 30° C.

TABLE 6

| Amount of produced β-phenyl-β-alanine | | |
|---|---|---|
| | E. intermedia | C. freundii |
| Produced β-phe (mM) | 1.3 | 4.4 |

Example 6

Production of Tryptophan (Trp) from $^{15}$N-labeled IPA-oxime ([15]N Isotope-Labeled indol-3-pyruvate oxime)

*Escherichia intermedia* AJ 2607 was cultured in the same manner as in Example 4 to obtain a wet microorganism cells. The resulting microorganism cells were inoculated onto the following reaction solution 12 such that the weight of the wet microorganism became about 1% (w/v), and then the reaction mixture was reacted at 30° C. for 24 hours.

Reaction solution 12: 100 mM glycine-NaOH (pH 9.0), 50 mM $^{15}$N-labeled IPA-oxime, 1 mM $MgCl_2$, 1 mM pyridoxal-5'-phosphate (PLP), 25 mM NADH, 25 mM NADPH, and 1% (v/v) toluene

[15]N-labeled IPA-oxime was prepared in accordance with the following procedure. 1.413 g (6.95 mmol) of indolpyruvic acid and 0.913 ml of 8 N NaOH were added to and dissolved in 60 ml of water at 25° C. in an argon stream. 0.5 g (7.09 mmol) of [15]$NH_2OH$ hydrochloride and 0.913 ml of 8 N NaOH were added to the solution and stirred at 25° C. for 1 hour. The pH was adjusted to 3 with 4.9 ml of 1 N hydrochloric acid and stirred at 25° C. overnight. The precipitated crystals were separated by filtration, and 2.07 g of the wet crystals were dried at 40° C. under reduced pressure, whereby 0.81 g (3.58 mmol) of $^{15}$N-labeled IPA-oxime (area purity, 97.5%) was obtained.

As a result of analysis of the reaction solution by LC-MS, a peak of +206 (corresponding to $^{15}$N) was detected in the $^{15}$N-labeled section, which indicates that oxime had been enzymatically reduced.

INDUSTRIAL APPLICABILITY

The present invention is useful for producing various amino acid derivatives.

The invention claimed is:

1. A method for producing an amino acid compound of formula (III), said method comprising:

contacting a microorganism with a hydroxyimino acid represented by formula (I):

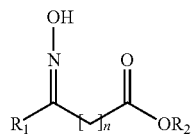

(I)

wherein $R_1$ represents a substituent selected from:
an optionally substituted C2 to C6 alkyl group,
an optionally substituted C6 to C14 aryl group,
an optionally substituted C6 to C10 cycloalkyl group,
an optionally substituted C7 to C19 aralkyl group,
an optionally substituted C2 to C10 alkoxyalkyl group,
an optionally substituted group which is identical with any one of the foregoing groups except for containing a heteroatom in the carbon skeleton thereof, and
a substituent $R_3$ represented by formula (II):

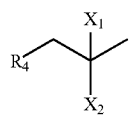

(II)

wherein $R_4$ represents a substituent selected from an optionally substituted C2 to C6 alkyl group, an optionally substituted C6 to C14 aryl group, an optionally substituted C6 to C10 cycloalkyl group, an optionally substituted C7 to C19 aralkyl group, an optionally substituted C2 to C10 alkoxyalkyl group, and an optionally substituted group which is identical with any one of the foregoing groups except for containing a heteroatom in the carbon skeleton thereof; $X_1$ and $X_2$ independently represent a hydroxyl group or a carbonyl group;

$R_2$ represents a C1 to C3 alkyl group or a hydrogen atom; and n is 0 or 1, to produce said amino acid compound represented by formula (III):

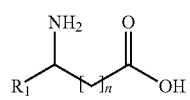

(III)

wherein $R_1$ and n have the same meanings as those of $R_1$ and n in formula (I), wherein said microorganism is capable of catalyzing a conversion of said hydroxyimino acid represented by formula (I) to said amino acid compound represented by formula (III), and wherein said microorganism is one or more members selected from the group consisting of *Citrobacter freundii*, *Escherichia intermedia*, *Escherichia coli*, and *Rhodococcus marinonascens*.

2. The method according to claim 1, wherein n is 0, and the amino acid compound produced thereby is an α-amino acid derivative.

3. The method according to claim 1, wherein the amino acid compound produced thereby is an α-L-amino acid.

4. The method according to claim 1, wherein the amino acid compound produced thereby is an α-D-amino acid.

5. The method according to claim 1, wherein n is 1, and the amino acid compound produced thereby is a β-amino acid derivative.

6. The method according to claim 1, wherein the aryl group is an optionally substituted phenyl or naphthyl group.

7. The method according to claim 1, wherein the aralkyl group is an optionally substituted phenylalkyl or naphthylalkyl group.

8. The method according to claim 1, wherein the group containing a heteroatom in the carbon skeleton is an optionally substituted pyridyl or indolyl group.

9. The method according to claim 1, wherein said microorganism is *Citrobacter freundii*.

10. The method according to claim 1, wherein one or more compounds selected from the group consisting of NADH, NADPH, pyridoxal-5'-phosphate, and MgCl$_2$ are added to a reaction solution for producing said compound represented by the general formula (III) from said compound represented by formula (I).

11. The method according to claim 1, wherein said microorganism is *Escherichia intermedia*.

12. The method according to claim 1, wherein said microorganism is *Escherichia coli*.

13. The method according to claim 1, wherein said microorganism is *Rodococcus marinonascens*.

14. A method for producing monatin, comprising contacting a microorganism with IHOG-oxime represented by formula (IV):

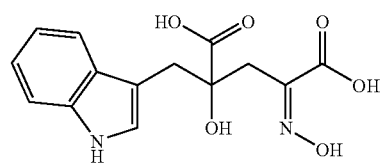

(IV)

to produce monatin represented by formula (V):

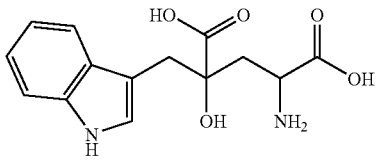
(V)

wherein said microorganism is capable of catalyzing a conversion of said IHOG-oxime represented by formula (IV) to said monatin, and wherein said microorganism is one or more members selected from the group consisting of *Citrobacter freundii, Escherichia intermedia, Escherichia coli*, and *Rhodococcus marinonascens*.

15. The method according to claim 14, wherein said microorganism is *Citrobacter freundii*.

16. The method according to claim 14, wherein one or more compounds selected from the group consisting of NADH, NADPH, pyridoxal-5'-phosphate, and MgCl$_2$ are added to a reaction solution for producing said monatin compound represented by formula (V) from said IHOG-oxime represented by formula (I) (IV).

17. The method according to claim 14, wherein said microorganism is *Escherichia intermedia*.

18. The method according to claim 14, wherein said microorganism is *Escherichia coli*.

19. The method according to claim 14, wherein said microorganism is *Rodococcus marinonascens*.

20. A method for producing β-phenyl-β-alanine, comprising contacting a microorganism with BAE-oxime represented by formula (VI):

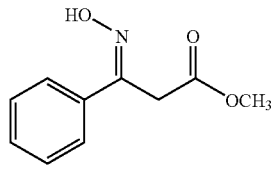
(VI)

to produce β-phenyl-β-alanine, wherein said microorganism is capable of catalyzing a conversion of said BAE-oxime represented by formula (VI) to said β-phenyl-β-alanine, and wherein said microorganism is one or more members selected from the group consisting of *Citrobacter freundii, Escherichia intermedia, Escherichia coli*, and *Rhodococcus marinonascens*.

21. The method according to claim 20, wherein said microorganism is *Citrobacter freundii*.

22. The method according to claim 20, wherein one or more compounds selected from the group consisting of NADH, NADPH, pyridoxal-5'-phosphate, and MgCl$_2$ are added to a reaction solution for producing said β-phenyl-β-alanine from said BAE-oxime represented by formula (VI).

23. The method according to claim 20, wherein said microorganism is *Escherichia intermedia*.

24. The method according to claim 20, wherein said microorganism is *Escherichia coli*.

25. The method according to claim 20, wherein said microorganism is *Rodococcus marinonascens*.

26. A method for producing tryptophan, comprising contacting a microorganism with indol-3-pyruvate-oxime represented by formula (VII):

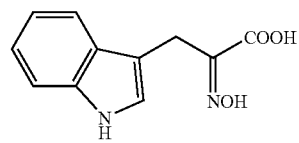
(VII)

to produce tryptophan, wherein said microorganism is capable of catalyzing a conversion of said indol-3-pyruvate-oxime represented by formula (VII) to said tryptophan, and wherein said microorganism is one or more members selected from the group consisting of *Citrobacter freundii, Escherichia intermedia, Escherichia coli*, and *Rhodococcus marinonascens*.

27. The method according to claim 26, wherein said microorganism is *Citrobacter freundii*.

28. The method according to claim 26, wherein one or more compounds selected from the group consisting of NADH, NADPH, pyridoxal-5'-phosphate, and MgCl$_2$ are added to a reaction solution for producing said tryptophan from said indol-3-pyruvate-oxime compound represented by formula (VII).

29. The method according to claim 26, wherein said microorganism is *Escherichia intermedia*.

30. The method according to claim 26, wherein said microorganism is *Escherichia coli*.

31. The method according to claim 26, wherein said microorganism is *Rodococcus marinonascens*.

* * * * *